(12) United States Patent
Thielen et al.

(10) Patent No.: US 6,315,775 B1
(45) Date of Patent: Nov. 13, 2001

(54) LIGHT DIFFUSING DEVICE FOR PHOTODYNAMIC TREATMENT OF ORGANS

(75) Inventors: Patrick Thielen, Genève; Alain Woodtli, Saint-Aubin, both of (CH)

(73) Assignee: Medlight S.A., Ecublens (CH)

( * ) Notice: Subject to any disclaimer, the term of this patent is extended or adjusted under 35 U.S.C. 154(b) by 0 days.

(21) Appl. No.: 09/297,360

(22) PCT Filed: Aug. 28, 1998

(86) PCT No.: PCT/CH98/00371

§ 371 Date: Apr. 30, 1999

§ 102(e) Date: Apr. 30, 1999

(87) PCT Pub. No.: WO99/11323

PCT Pub. Date: Mar. 11, 1999

(30) Foreign Application Priority Data

Sep. 4, 1997 (FR) .................................................. 97 11254

(51) Int. Cl.⁷ .................................................. A61B 18/18
(52) U.S. Cl. .................................. 606/16; 606/15; 607/89; 362/558
(58) Field of Search .................................. 606/2, 7, 9, 10, 606/13–18; 607/88, 89, 93; 385/123–125, 141, 142, 144; 362/32, 558

(56) References Cited

U.S. PATENT DOCUMENTS

| | | |
|---|---|---|
| 4,733,332 * | 3/1988 | Yamashita et al. .................. 362/32 |
| 5,207,669 * | 5/1993 | Baker et al. .......................... 606/7 |
| 5,431,647 * | 7/1995 | Purcell et al. ....................... 606/16 |
| 5,536,265 | 7/1996 | Van den Bergh . |

FOREIGN PATENT DOCUMENTS

| | | |
|---|---|---|
| WO 90 00914 A | 2/1990 | (WO) . |
| WO 93 25155 A | 12/1993 | (WO) . |
| WO 96 07451 A | 3/1996 | (WO) . |
| WO 97 07735 A | 3/1997 | (WO) . |

* cited by examiner

*Primary Examiner*—Roy Gibson
(74) *Attorney, Agent, or Firm*—Nixon & Vanderhye P.C.

(57) ABSTRACT

A light diffusing device for the irradiation of biological tissues in photodynamic treatment includes a light guide having an unclad section at its distal tip, the unclad section being surrounded with at least one layer of diffusing substance for diffusing the light circulating in the light guide. The diffusing layer includes a prefabricated tubular piece having walls of constant thickness in which the unclad section is inserted.

14 Claims, 1 Drawing Sheet

LIGHT DIFFUSING DEVICE FOR PHOTODYNAMIC TREATMENT OF ORGANS

Figure 1:
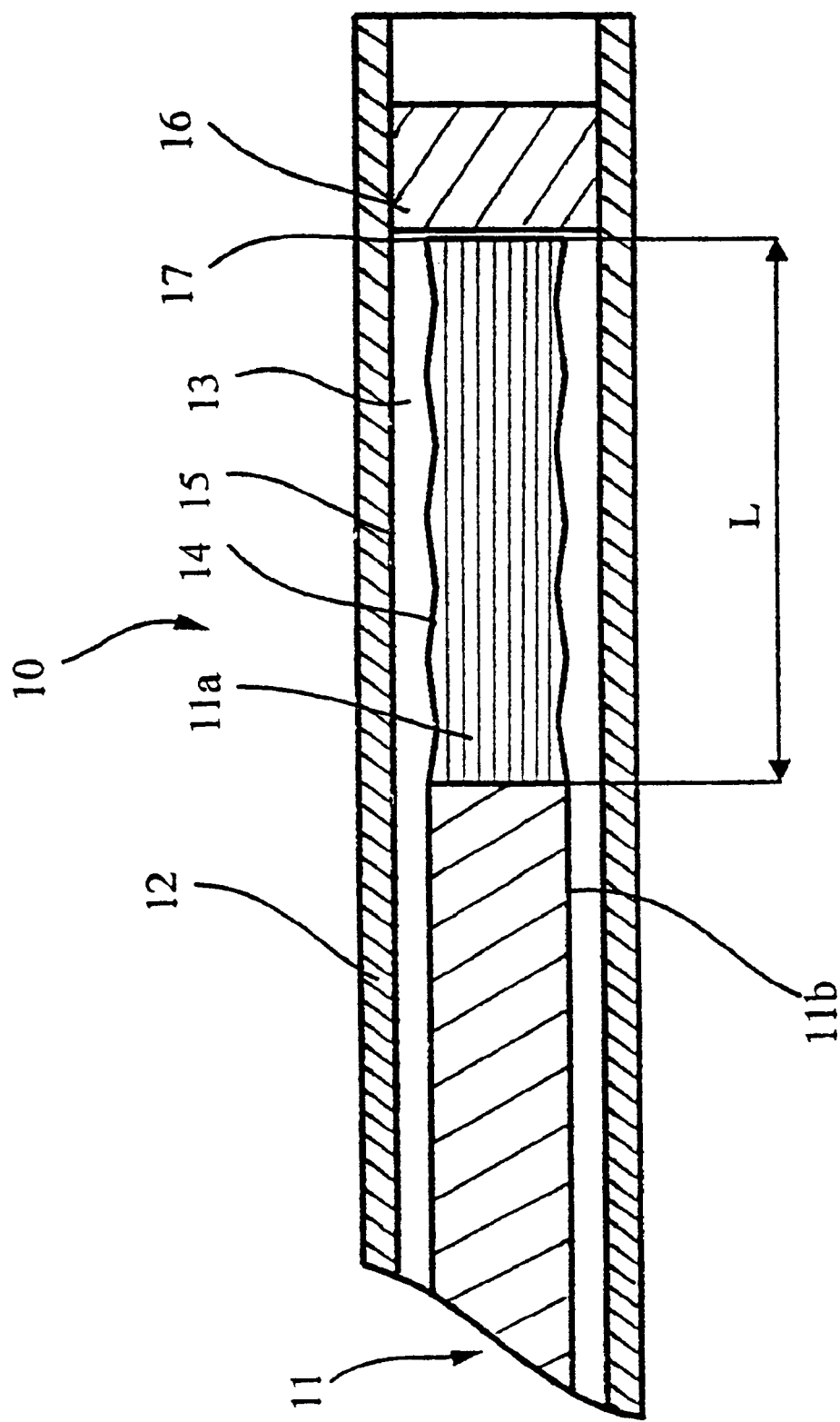

This application is a 371 of PCT/CH98/00371, filed Aug. 28, 1998.

TECHNICAL DOMAIN

The current invention relates to an appliance for light diffusion designed specifically for the irradiation of biological tissues during photodynamic therapy. This appliance is comprised of a light conductor, in particular a fiber optic with a section at its tip exposed to the core, with the section surrounded by at least one layer of diffusing substance with the ability to diffuse the light circulating in said light conductor.

PREVIOUS TECHNIQUE

In the photodynamic treatment of cancerous surface lesions or other pathological diseases in human body organs, the technique currently being used consists of intravenously injecting a sensitizer which becomes localized particularly in neoplastic tissues. The part of the diseased tissue containing the photosensitizer is then irradiated with a light, the wavelength of which is decided by the photosensitizer injected. This light activates the photosensitizer and causes a chemical reaction which destroys the cells. This irradiation is implemented with the help of flexible diffusers guiding the light which generally originates from a laser source and they diffuse this light in the organ undergoing treatment in a controlled way. The intensity of the light emitted by the diffuser must be homogeneous over the entire surface to be treated in order to avoid problems linked with over- or under-exposure. Over-exposure caused by strong luminous power can cause damage to adjacent healthy tissues as well as local heating. Under-exposure can lead to a recurrence of the illness if specific cells are not killed by the treatment.

Several diffusers of this type are known, in particular the light diffuser described in American patent U.S. Pat. No. 5,536,265. This diffuser is comprised of a fiber optic with a section at its tip exposed to the core, a first layer of a flexible transparent substance, a second layer of a material capable of diffusing light, all of this contained in a transparent tubular part which forms a protective casing.

On the one hand, this diffuser is of complex design. On the other hand, the fiber optic section at the tip, which can reach around 10 centimeters with a diameter of several hundred microns, is extremely difficult to center inside a tubular part because of the flexibility of these two elements. As a result, the second layer, which is made from a material with diffusing properties, is irregular around the exposed fiber core which forms the section at the tip. However, diffusing properties are linked, in particular, with the thickness of the diffusing matter surrounding the core.

In order to obtain a homogeneous diffusion of the light transmitted by the fiber optic, it is essential for the diffusing particles to be distributed in a homogeneous way and that the thickness of the diffusing layer remains constant.

DESCRIPTION OF THE INVENTION

The aim of the current invention is to eliminate these drawbacks of the previous method by providing a diffusing appliance which addresses this objective and which is of simplified design. For this purpose, the appliance according to the invention is characterized by the fact that the layer of light diffusing substance is comprised of a tubular manufactured part with walls of a consistent thickness to which the fiber tip section is attached.

In accordance with a more beneficial manufacturing process, this tubular part is made of a thermoformable material which incorporates diffusing particles that are able to diffuse light. These particles are distributed homogeneously throughout this thermoformable material.

Ideally it will include a layer of transparent material positioned between the external face of the tip section and the internal wall of the tubular part.

As a benefit the appliance can include at its distal extremity a mirror arranged to reflect light emanating from the fiber tip section into the fiber.

The tubular part is preferably manufactured by extrusion from a long tubular segment of thermoformable material containing diffusing particles and by cutting to size a section of predetermined length.

The tubular part with the diffusing properties will ideally form the external protective casing of the fiber optic section.

CONCISE DESCRIPTION OF THE DRAWINGS

The current invention will be better understood in reference to the description of a preferred design example and the drawing appended in which FIG. 1 represents a cross-section of the tip of the diffusing appliance according to the invention.

BEST METHOD OF PRODUCING THE INVENTION

With reference to FIG. 1, the tip of the diffusing appliance (10) is comprised of a fiber optic (11) made up of a core (11a) surrounded by a covering (11b), placed in a tubular part forming a protective casing (12). This fiber section (11) is held in position in the protective casing (12) by a layer of a material (13) placed between the external wall (14) of the fiber section (11) and the internal wall (15) of the protective casing (12). A mirror (16) fitted into the casing (12) is flattened against the surface of the tip (17) of the fiber section (11) and forms the distal tip of the diffuser (10).

To produce this diffuser (10), in an initial step, the covering (11b) of the fiber (11) is destroyed over a length L corresponding to the length of the diffusing part of the diffuser (10) in order to allow some of this light to escape from the core of the fiber. When this part of the covering has been removed, the core part (11a) thus laid bare is roughened.

This roughness can be achieved in different ways, for example
- by attacking with a chemical substance with the help of an acid, a base or a solvent
- by attacking mechanically by abrasion, sanding or removal of chippings
- by thermal attack using hot air, a heated tool or thermal laser or
- by laser machining using an excimer laser.

The method used should permit control of the roughness so that the amount of light which thus escapes from the core (11a) of the fiber along length L corresponds to the desired profile.

In a second stage, the section of the fiber (11) laid bare is fitted into an external casing (12). This casing is intended, firstly, to protect the fiber from being affected by external agents, such as the chemical products used to disinfect the diffuser prior to use and mechanical shocks which could occur during manipulation and, secondly, to homogenize the angular distribution of light escaping from the roughened part of the fiber which is subject to the phenomena of diffraction and refraction.

In order to obtain this homogenization, the casing is made of a thermoplastic material which is embedded with particles of a diffusing substance, the aim of these particles being to diffract and/or refract the light emitted by the section of fiber (11) and to make it homogeneous. The substance used is, for example, titanium dioxide ($TiO_2$), which is incorporated into the thermoplastic material in the ratio of around 1% of its weight. The preparation of the mixture of the diffusing substances and the thermoplastic material can be done in relatively large volumes industrially in order to obtain a homogeneous distribution of the particles. This mixture is then extruded and a segment the length of the casing is thermoformed in the usual way.

The casing (12) thus obtained has a constant thickness of diffusing matter and can be manufactured with great precision. The casing sections usable for the production of diffusing appliances are cut off along their lengthwise segments which also permits the guarantee of constancy of optical characteristics of the sections thus obtained.

The fiber (11) is held in the casing (12) by means of a layer (13) of a transparent connecting material introduced between the external wall (14) of the section of fiber (11) and the internal wall (15) of the casing (12). The material generally used is transparent silicone rubber as this provides excellent optical transmission. Its refractive index is lower to that of the fiber core and its mechanical properties are well known. Nevertheless, the use of any other flexible, transparent material in which the refractive index is weak could be considered. The thickness of the layer (13) is not a key factor in the production of the diffuser according to this invention since a thickness of around 630 nm is sufficient to guarantee the guiding wavelength effect required. Thanks to its weak refractive index, this layer acts as a covering for the exposed core (11a) of the section tip of the fiber (11).

The mirror (16) whose reflective surface is pressed against the tip surface (17) of the fiber section (11) allows the loss of light at the fiber tip to be limited by reflecting light emitting from the tip surface (17) back into the diffusing part.

The benefit of a diffuser of this type in relation to the one in the American patent mentioned at the beginning is that the thickness of the diffusing material remains constant since making a casing by means of extrusion of a thermoplastic material is well controlled. In the diffuser of the previous type, the thickness of the diffusing material was dependent on centering the fiber in the external casing which is very difficult to control given that the fiber and the external casing are flexible and that centering has to be achieved over a length that can be anything up to 10 cm. There is a great probability that the fiber will touch the external casing at one point which will result in having a very weak thickness of diffusing material at this point of contact and thus inferior light diffusion. In the diffuser in this invention, centering of the fiber in the casing is not critical since the thickness of the transparent layer (13) does not influence the back-scattering of the light in a significant way. In addition, the design of this diffuser is simplified since the casing (12) which is produced in a standard way acts as an external protective casing while still diffusing and thus allows the omission of an intermediate layer.

In alternative design solutions, the casing could be thermoformed directly around the fiber. The layer of transparent material could also be replaced by a layer of air and the fiber could be attached to the casing to the internal casing wall solely by adhesive placed at regular intervals.

What is claimed is:

1. A light diffusing device for the irradiation of biological tissues in photodynamic treatment, the diffusing device comprising a light guide having an unclad section at a distal end thereof, the unclad section being roughened and surrounded with at least one layer of a diffusing substance for diffusing the light circulating in the light guide, the diffusing layer comprising a preformed tubular piece having walls of constant thickness in which the unclad section is inserted, no other diffusing layer being placed between the unclad section and the preformed diffusing layer.

2. The device according to claim 1, wherein the preformed tubular piece is made of a thermoformable material into which diffusing particles are incorporated, the particles being spread homogeneously throughout the thermoformable material.

3. The device according to claim 2, wherein the preformed tubular piece is obtained by the extrusion of a long tubular segment of thermoformable material containing diffusing particles, and by cutting off a section of predetermined length.

4. The device according to claim 3, wherein the extruded material is comprised of around 1% in weight of diffusing particles.

5. The device according to claim 1, further comprising a layer of transparent material positioned between an external wall or the unclad section and an internal wall of the preformed tubular piece.

6. The device according to claim 1, further comprising a mirror arranged to reflect light emitted from the unclad section of the light guide back into the light guide.

7. The device according to claim 1, wherein the preformed tubular piece with diffusing properties forms an external protective casing for the unclad section of the light guide.

8. The device according to claim 1, wherein the light guide comprises an optical fiber.

9. A light diffusing device for the irradiation of biological tissues in photodynamic treatment, comprising:

a light guide having a roughened unclad section at a distal end thereof; and an outer, external tube surrounding the unclad section of the light guide, the outer external tube having walls of uniform thickness and having embedded therein particles of a diffusing substance for diffusing light circulating in the light guide.

10. The light diffusing device according to claim 9, further comprising:

a transparent layer arranged between the unclad section of the light guide and the outer, external tube.

11. The light diffusing device according to claim 10, wherein the transparent layer comprises silicone rubber.

12. The light diffusing device according to claim 9, wherein the light guide comprises an optical fiber.

13. The light diffusing device according to claim 9, wherein the particles of a diffusing substance comprise particles of titanium dioxide.

14. The light diffusing device according to claim 9, wherein no light diffusing layer is disposed between the unclad section of the light guide and the outer, external tube.

* * * * *